(12) United States Patent
Oberreit

(10) Patent No.: US 10,551,292 B2
(45) Date of Patent: Feb. 4, 2020

(54) COLLOID PARTICLE SIZE-MASS DISTRIBUTION MEASUREMENT TECHNOLOGY

(71) Applicant: Derek Oberreit, Roseville, MN (US)

(72) Inventor: Derek Oberreit, Roseville, MN (US)

(73) Assignee: Kanomax FMT, Inc., White Bear Lake, MN (US)

( * ) Notice: Subject to any disclaimer, the term of this patent is extended or adjusted under 35 U.S.C. 154(b) by 238 days.

(21) Appl. No.: 15/638,537

(22) Filed: Jun. 30, 2017

(65) Prior Publication Data

US 2018/0284005 A1 Oct. 4, 2018

Related U.S. Application Data

(60) Provisional application No. 62/356,619, filed on Jun. 30, 2016.

(51) Int. Cl.
*G01N 15/02* (2006.01)

(52) U.S. Cl.
CPC ..... *G01N 15/0266* (2013.01); *G01N 15/0255* (2013.01); *G01N 2015/0294* (2013.01)

(58) Field of Classification Search
CPC ........... G01N 15/0255; G01N 15/0266; G01N 2015/0038; G01N 2015/0294
See application file for complete search history.

(56) References Cited

U.S. PATENT DOCUMENTS

| | | | | |
|---|---|---|---|---|
| 5,247,842 A | * | 9/1993 | Kaufman | B05B 5/002 356/37 |
| 6,567,157 B1 | * | 5/2003 | Flagan | G01N 1/2247 356/335 |
| 9,086,350 B2 | * | 7/2015 | Grant | G01N 1/4022 |
| 9,625,365 B2 | * | 4/2017 | Ho | B01F 11/0071 |
| 2008/0137065 A1 | * | 6/2008 | Oberreit | G01N 30/84 356/37 |
| 2015/0330886 A1 | * | 11/2015 | Ho | B01F 11/0071 356/336 |
| 2017/0065941 A1 | * | 3/2017 | Ho | B01F 11/0071 |

* cited by examiner

*Primary Examiner* — Francis C Gray
(74) *Attorney, Agent, or Firm* — Skinner and Associates; Joel Skinner

(57) ABSTRACT

A system and method for measuring particle mass distributions as a function of particle diameter. The system includes a nebulizer, a particle size classifier and a particle detector. The system may include a dilution module. It may also include a particle mass classifier. The system and method are useful for distinguishing particle populations of similar size and different densities as well as determining the interaction between materials (binding) in mixed colloid systems with varying material ratios. The system and method are also useful for determining particle density in both homogeneous and heterogeneous colloids.

18 Claims, 10 Drawing Sheets

$$N_{ij} = \sum_{z=1}^{6} \int \int_0^\infty \int_0^\infty A_i(z,d_p)\Theta_j(z,d_p)\epsilon_{CPC}(d_p,m_p)\epsilon_{CPC}(d_p)\epsilon_T(d_p)f(z,d_p)\frac{\partial^2 n}{\partial d_p \partial m_p}dd_p dm_p$$

COLLOID PARTICLE SIZE-MASS DISTRIBUTION MEASUREMENT TECHNOLOGY

CROSS-REFERENCE TO RELATED APPLICATIONS, IF ANY

This application claims the benefit under 35 U.S.C. § 119(e) of U.S. Provisional Patent Application Ser. No. 62/356,619, filed Jun. 30, 2016, which is hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to analysis methods and apparatus for analyzing material. Particularly, the invention relates to measuring properties of a colloid containing heterogeneous particle populations. Most particularly, the invention relates to measuring the particle mass distributions as a function of particle diameter. The technology is useful for distinguishing particle populations of similar size and different densities as well as determining the interaction between materials (binding) in mixed colloid systems with varying material ratios. The technology is also useful tor determining particle density in both homogeneous and heterogeneous colloids.

2. Background Information

Existing methods fall into two categories: in-situ where the particles remain suspended in a liquid, and ex-situ where the particles are dispersed in the gas phase.

In-situ technology measures the change in the peak diameter of the primary particle size distribution using light scattering or light dispersing (LD) methodologies. This technology is limited to particles greater than 10 nm using single particle detection as is the ease with Particle Tracking (PT) and Laser Diffraction (LD). Dynamic Light Scattering (DLS) methodology is capable of measuring size distributions for smaller particles but is unable to directly resolve bi-modal systems that are present m heterogeneous aggregation studies. PT and DLS methods are dependent on dispersant temperature and viscosity. LD methods are dependent on particle and dispersant retractive indices.

Ex-situ methods aerosolize the colloid particles either by electrospray ionization (ESI) or by purely mechanical nebulization (pneumatic, ultrasonic, and Rayleigh breakup). The particle properties then measured by measuring the size and or mass of the particles using established techniques. Generally, the colloids under study will contain a dissolved, non-volatile solute either as an artifact from the colloid synthesis process, intentionally added to modify the properties of the continuous phase (e.g. pH adjustment), or to stabilize the colloid by limiting coagulation. The presence of this solute leads to the formation of discrete particles consisting entirely of the solute and also coats the surface of the aerosolized particles. Specifically, systems used to measure diameter and or mass of colloids utilizing aerosolization are adversely affected by the presence of dissolved, non-volatile residue in the sample.

The devices and method of the present invention mitigate the effect of this residue through online dilution of the sample immediately prior to aerosolization. Additionally, the properties of heterogeneous colloids (containing particles of multiple materials, sizes, and or densities) often vary as a function of the relative particle and or solute concentrations. The online dilution process also limits the time allowed to undergo changes in the particle properties as a result of dilution. The use of tandem Size-Mass measurement systems facilitates both separation of similarly sized particles with different densities as well as density information.

Existing technology in this field is believed to have significant limitations and shortcomings. For this and other reasons, a need exists for the present invention.

All US patents and patent applications, and all other published documents mentioned anywhere in this application are incorporated by reference in their entirety.

BRIEF SUMMARY OF THE INVENTION

The invention provides an analysis apparatus and method which are practical reliable, accurate and efficient, and which are believed to fulfill a need and to constitute an improvement over the background technology.

The use of nanoparticles in industrial and medical applications has increased the need for instrumentation and methods to study their physical properties (size, shape, concentration, and density). Specifically, researchers are interested in the particle size and density distributions of nanoparticles prepared in liquid suspensions (colloids). To utilize high-precision, aerosol-based measurement methods, these colloidal samples must first be aerosolized. Several established techniques have been employed to aerosolize colloidal particles; however, these methods are sensitive to sample purity, require extensive method development, are unstable over long periods, or lack effective data inversion routines to calculate the true mass and size distributions.

The invention presents a method for analyzing nanoparticle size and mass distributions that couples a new colloidal nanoparticle aerosolization device to a aerosol mass analyzer and a portable aerosol electrical mobility analyzer. The system preferably uses a data inversion algorithm.

The system of the invention includes an aerosolization device which creates fine droplets of the fluid (nebulization) containing particles and dissolved material. In one aspect, the particles and dissolved material are at concentrations equal to the sample.

In another aspect, the particles and dissolved material are diluted online with a high purity dispersant immediately prior to nebulization. Upon evaporation of the liquid, the gas-borne droplet becomes either a particle consisting of non-volatile precipitated material or becomes a particle consisting of a colloid particle/aggregate and non-volatile precipitated material. At the residue concentrations and particle sizes of interest, online dilution aids in reducing the size of the residue particles and the degree of residue contamination. In one aspect the colloid particle size distributions are quantified by measuring aerosol particle properties which are a function of the particle size (e.g. electrical mobility).

In another aspect, the colloid particle mass distribution is quantified by measuring aerosol particle properties which are a function of the particle mass (e.g. centrifugal/electrostatic force balance).

In another aspect, the colloid particle properties may be measured by measuring the mass distribution at various selected particle sizes using the respective spectrometers in tandem.

In another aspect the colloid particle properties may be measured by measuring the size distribution at various selected particle masses using the respective spectrometers in tandem. The particle size distribution may be measured using a Scanning Mobility Particle Sizer (SMPS) system, the mass distribution may be measured using an Aerosol Particle Mass (APM) analyzer or a mass spectrometer. These systems also have the capability of selecting specific sizes and masses for sampling by another instrument.

The aspects, features, advantages, benefits and objects of the invention will become clear to those skilled in the art by reference to the following description, claims and drawings.

DETAILED DESCRIPTION

Colloidal suspensions of nanoparticles will often contain dissolved non-volatile residue (DNVR) composed of surfactants and or salts that are required for stabilization and/or are by-products of the manufacturing process. Upon aerosolization of the colloid, the DNVR may substantially alter the size and/or properties of the aerosolized colloid particles (by precipitation onto the particle surface), as well as form aerosol particles composed entirely of precipitated NVR (which are indistinguishable from the colloidal particles). The invention utilizes a nanoparticle aerosolizer utilizing pneumatic nebulization, which is used to aerosolize colloidal mixtures for gas phase analysis.

Figure 10:
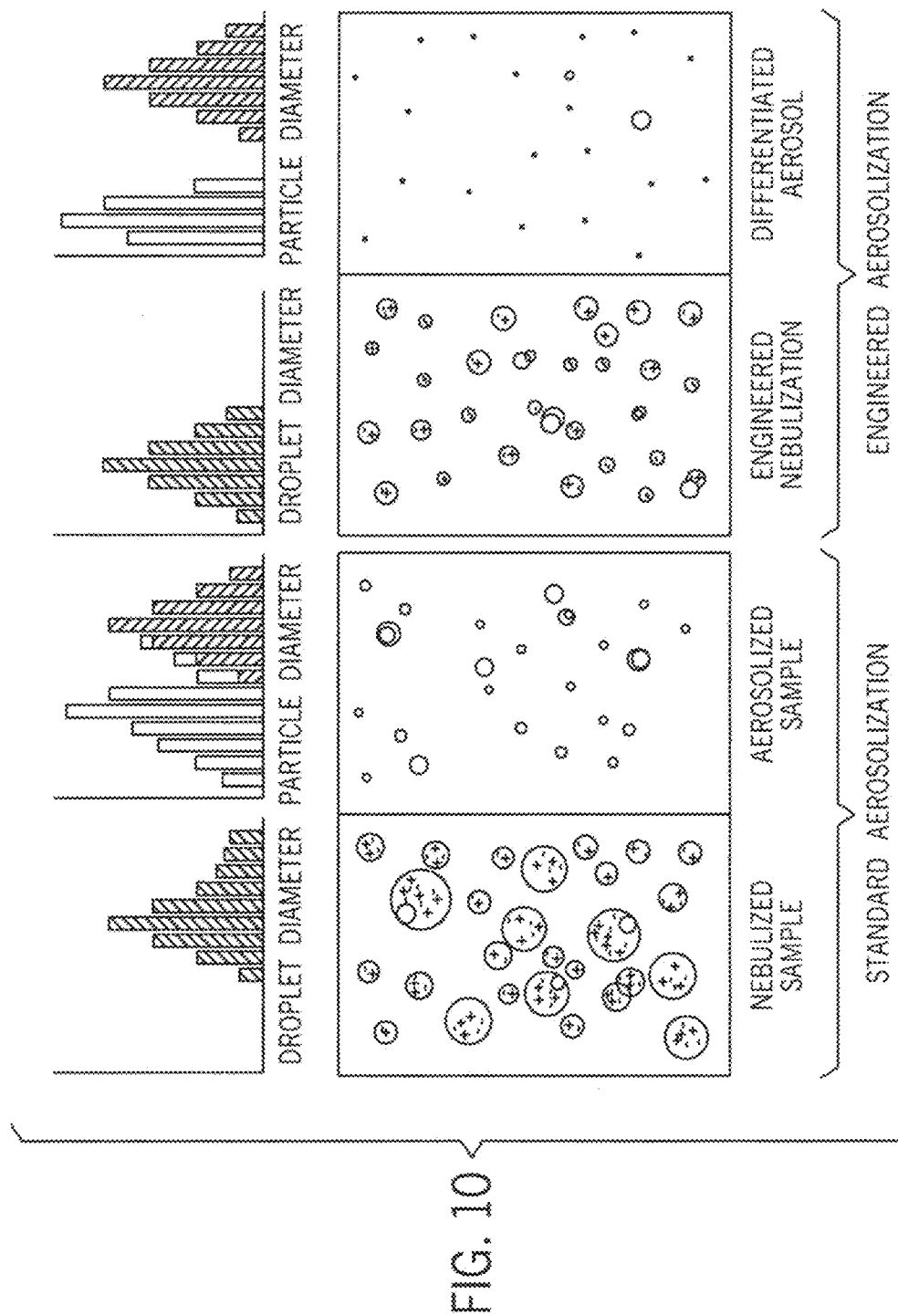
FIG. 10 illustrates varying composition or shape (fractal dimension) properties of colloidal suspensions.

Referring to FIG. 10, colloidal suspensions often contain particles with varying composition or shape (fractal dimension) properties. By measuring the particle size distributions at varying selected particle mass intervals, a two-dimensional array of the size and mass distributions can be generated. This dataset, along with appropriate data inversion, can provide density information for the particles in the sample, as well as distinction between the particle populations. While tandem mass and mobility measurements of colloidal particles has been done using standard high-resolution aerosol measurement equipment, the size and cost limits the broad application of this method. A lower cost, semi-portable, system is needed to facilitate the application of this method.

Figure 1:
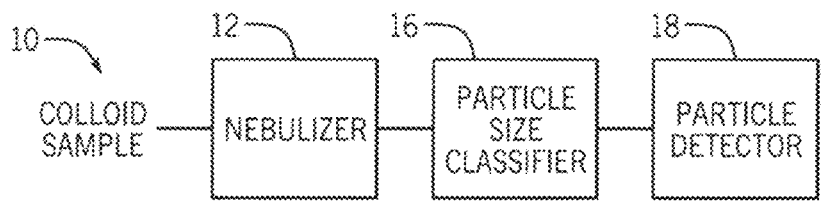
FIG. 1 is a schematic representation of an embodiment the system of the invention comprising a nebulizer and a particle size spectrometer consisting of a particle size classifier and particle detector.

FIG. 1 is a schematic representation of an embodiment the colloid particle size-mass distribution measurement system 10 of the present invention. The system 10 comprises a nebulizer 12 and a particle size spectrometer (PSS) 14. The particle size spectrometer comprises a particle size classifier 18 and a particle detector 20. This embodiment of the system does not utilize online dilution.

In use, a colloid sample is input to the nebulizer 12. The nebulizer 12 aerosolizes the input colloid sample creating line droplets of fluid containing panicles and dissolved material. In one example of use, the particles and dissolved material are at concentrations equal to the sample. Upon evaporation of the liquid, the gas-borne droplet becomes either a particle consisting of non-volatile precipitated material or the droplet becomes a particle consisting of a colloid particle/aggregate and non-volatile precipitated material. The colloid particle size distributions are quantified by measuring aerosol particle properties which are a function of the particle size (e.g. electrical mobility). The colloid particle mass distribution is quantified by measuring aerosol particle properties which are a function of the particle mass (e.g. centrifugal/electrostatic force balance).

Alternatively, the colloid particle properties may be measured by measuring the mass distribution at various selected particle sizes using the respective spectrometers in tandem. In yet another alternative, the colloid particle properties may be measured by measuring the size distribution at various selected particle masses using the respective spectrometers in tandem.

The particle size distribution may be measured using a Scanning Mobility Particle Sizer (SMPS) system. The mass distribution may be measured using an Aerosol Particle Mass (APM) analyzer, or a mass spectrometer. These systems also have the capability of selecting specific sizes and masses for sampling by another instrument.

Figure 2:
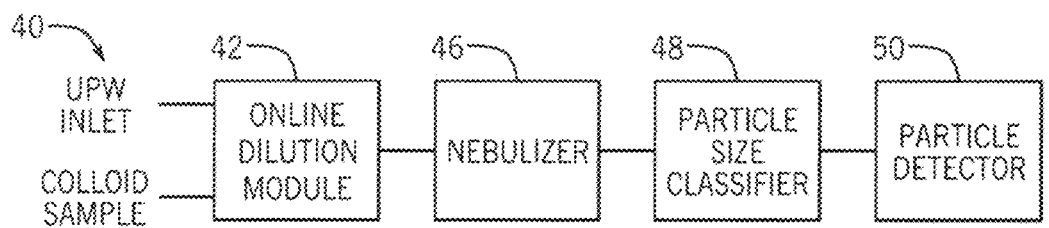
FIG. 2 is a schematic representation of an embodiment of the system of FIG. 1, including an online dilution means.

FIG. 2 is a schematic representation of a variant of the system 20 shown in FIG. 1, including online dilution. The system 40 comprises an online dilution module 42, a nebulizer 44 and a particle size spectrometer 46 including a particle size classifier 48 and a particle detector 50. In this embodiment, the particles and dissolved material are diluted online with a high purity dispersant immediately prior to nebulization. At the residue concentrations and particle sizes of interest, online dilution aids in reducing the size of the residue particles and the degree of residue contamination.

Figure 3:
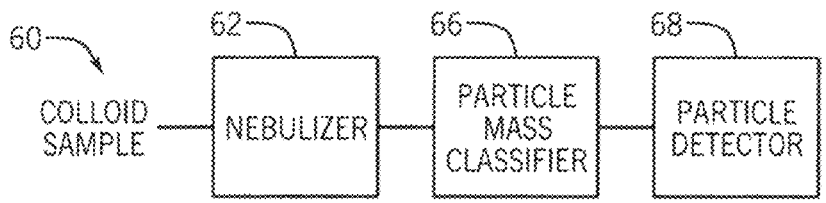
FIG. 3 is a schematic representation of an alternative embodiment of the system including a nebulizer and a particle mass spectrometer consisting of a particle mass classifier and a particle detector.

FIG. 3 is a schematic representation of an alternative embodiment of the system of the invention. The system 60 includes a nebulizer 62 and a particle mass spectrometer (PMS) 64. The PMS 64 includes a particle mass classifier 66 and a particle detector 68.

Figure 4:
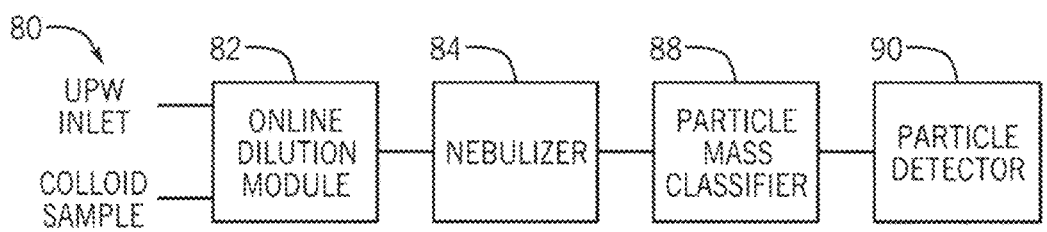
FIG. 4 is a schematic representation of the system of FIG. 3, with online dilution.

FIG. 4 is a schematic representation of a variant of the system 60. The system 80 comprises an online dilution module 82, a nebulizer 84, and a particle mass spectrometer 86, including a particle mass classifier 88 and particle detector 90.

Figure 5:
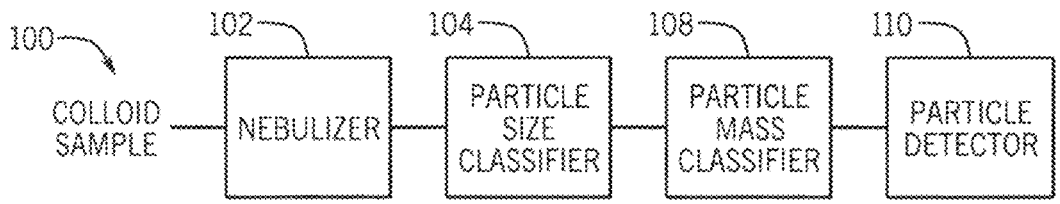
FIG. 5 is a schematic representation of another alternative embodiment, of the system including a nebulizer, a particle size classifier and a mass spectrometer including a particle mass classifier and a particle detector. The particle size classifier may alternatively be placed downstream of the particle mass classifier.

FIG. 5 is a schematic representation of another alternative embodiment of the system 100. The system 100 comprises a nebulizer 102, a particle size classifier 104 and a particle mass spectrometer 106. The PMS 106 includes a particle mass classifier 108 and a particle defector 110. In a variant of this embodiment (not shown), the size classifier 104 may be placed downstream of the mass classifier 108.

Figure 6:
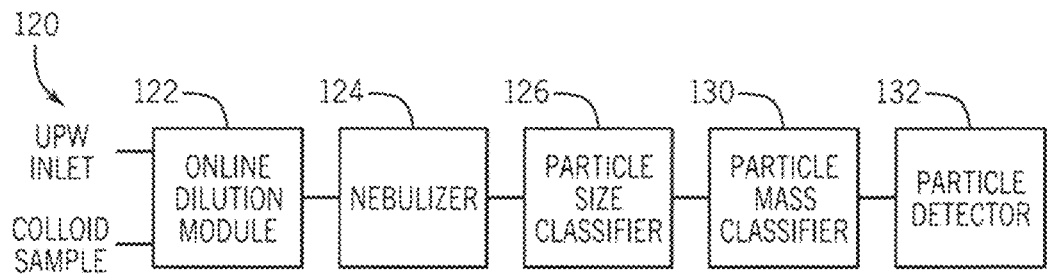
FIG. 6 is a schematic representation of the system of FIG. 5 with online dilution.

FIG. 6 is a schematic representation of a variant of the system 100. The system 120 includes an online dilution module 122, a nebulizer 124, a particle size classifier 126 and mass a particle mass spectrometer 128 (including a particle mass classifier 130 and a particle detector 132). The size classifier 126 may be placed downstream of the mass classifier 130.

Figure 7:
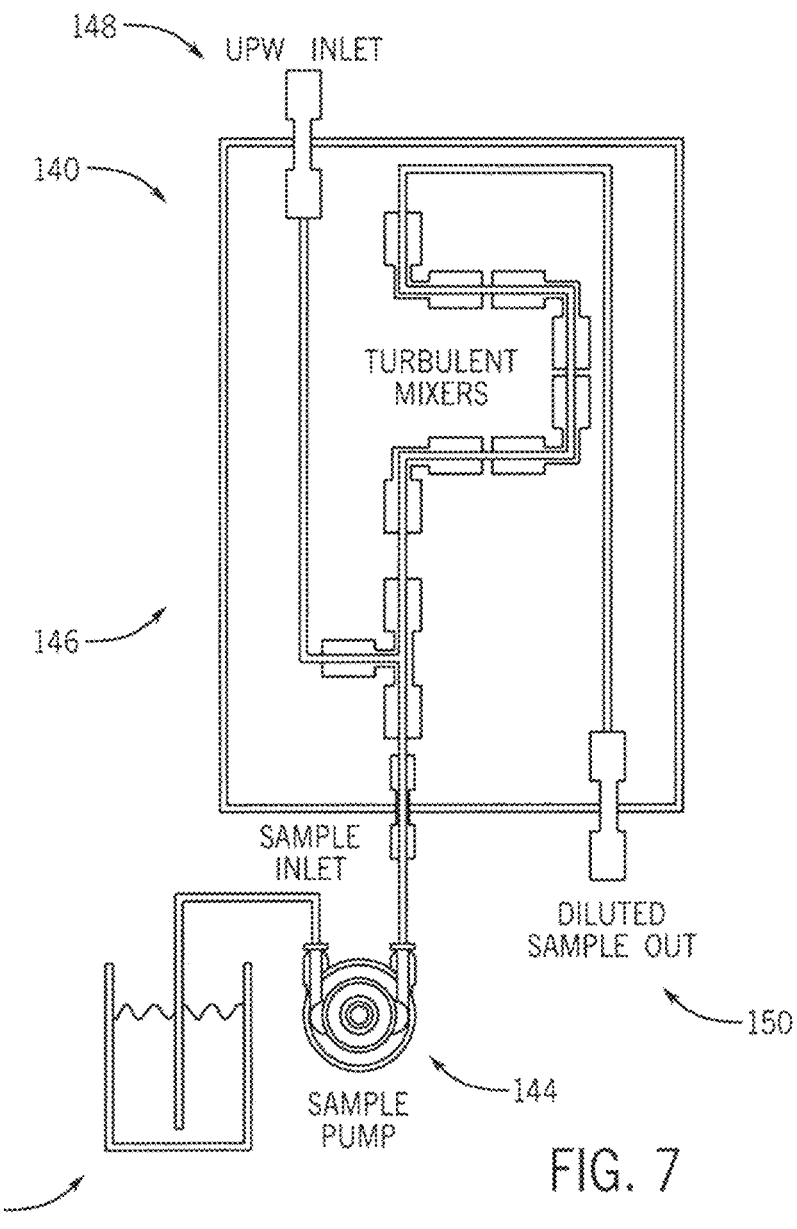
FIG. 7 is a schematic diagram of an embodiment of an online dilution means useable with the systems of the invention.

FIG. 7 is a schematic diagram of an embodiment of an on line dilution module or assembly 140, useable with the systems described above. The dilution system 140 comprises a fluid source 142, a sample pump 144, a plurality of turbulent mixers 146, and a sample outlet 150, connected in line. An ultra pure water (UPW) inlet 148 is communicatively connected to the mixer array 146.

Figure 8:
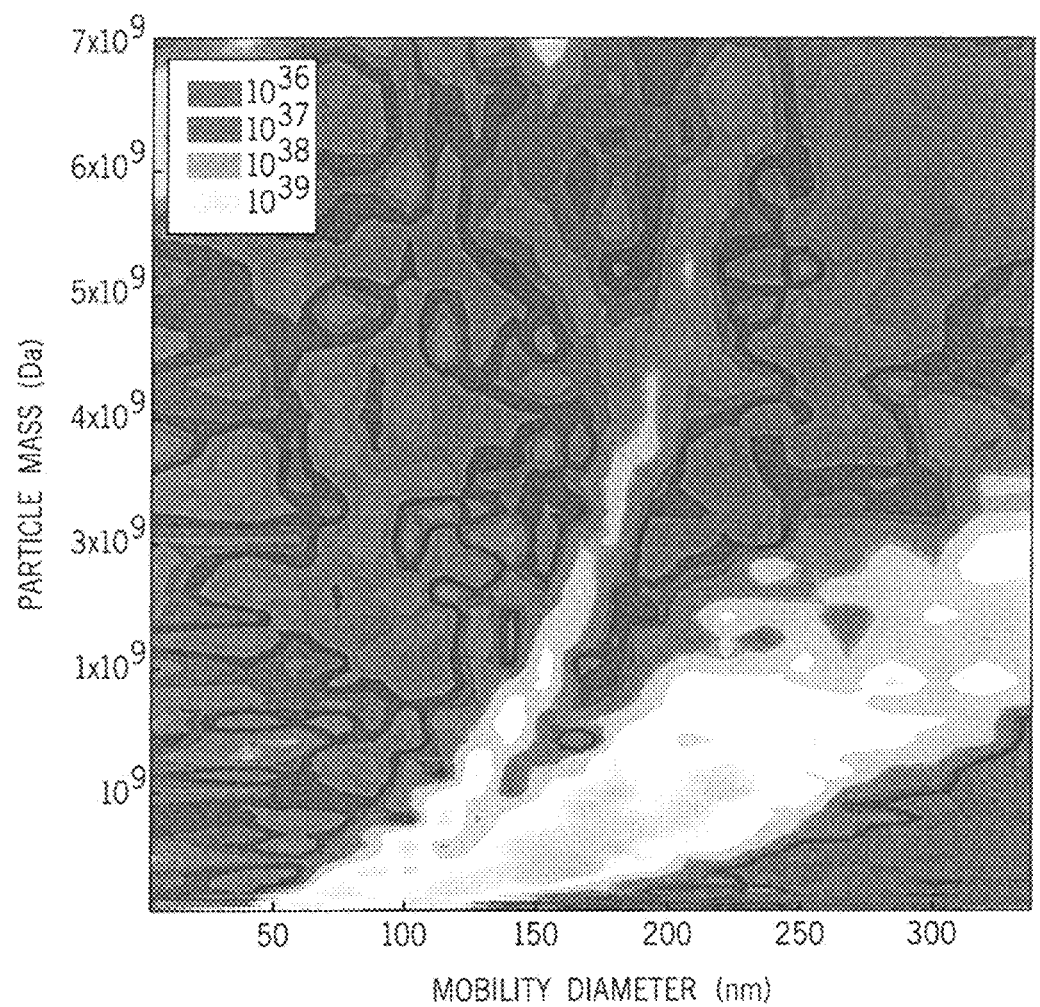
FIG. 8 is an example 2D particle size and mass distributions for a two component aerosol comprised of ammonium sulfate and soot.

FIG. 8 is an example 2D particle size and mass distributions for a two component aerosol comprised of ammonium sulfate and soot.

Nebulizers and mass analyzer systems that are useable in the embodiments of the invention are described in the following publications:
1. TAJIMA, Naoko, et al. (2011): Mass flange and Optimized Operation of the Aerosol Particle Mass Analyzer, *Aerosol Science and Technology*, 45:2, 196-214.
2. Seongho Jeon, Derek R. Oberreit, Gary Van Schooneveld, and Christopher J. Hogan, Jr. (2016): Nanomaterial size distribution analysis via liquid nebulization coupled with ion mobility spectrometry (LN-IMS), *Analyst*, 141, 1363.
3. Jeon Seongho, Derek Oberreit, Gary Van Schooneveld, and Christopher Hogan, Liquid Nebulization-Ion Mobility Spectrometry Based Quantification of Nanoparticle-Protein Conjugate Formation, Submitted for publication (2016) to *Analytical Chemistry*.

Figure 9:
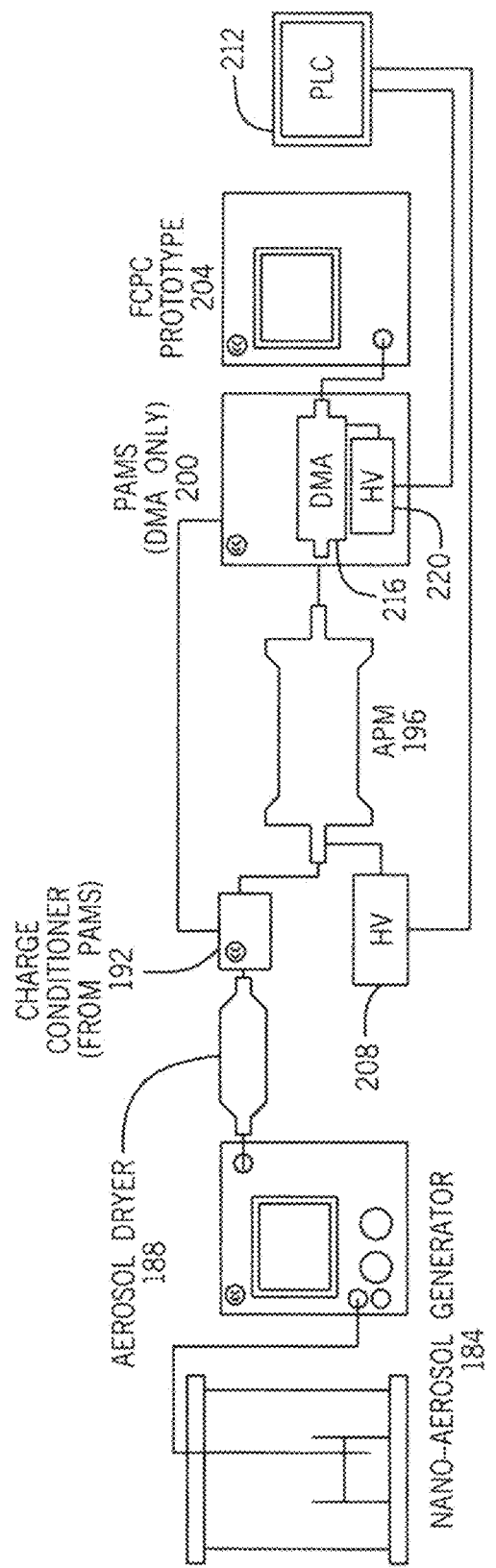
FIG. 9 illustrates another embodiment of the system of the invention.

FIG. 9 illustrates a further embodiment of the analyzer system of the invention. The system 180 utilizes the basic architecture of the system embodiment shown in FIG. 5, wherein the size classifier is placed downstream of the mass classifier. The system 180 comprises a Nano-aerosol generator (NAG) 184, an aerosol dryer 188, a charge conditioner 192, an aerosol particle mass analyzer (APMA) 196, a portable aerosol mobility spectrometer (PAMS) 200, and a condensation particle counter (CPC) 204. A high voltage module (HVM) 208 is communicatively connected to the APMA 196. The HVM 208 and PAMS 200 are communicatively connected to a program logic controller (PLC) 212. The NAG 184 aerosolizes a colloid sample. It utilizes a pressurized chamber to deliver sample at a steady rate. Operational conditions are fixed, and do not vary with sample composition. The charge conditioner 192 is disposed downstream of the aerosol dryer 188 connected to the output of the NAG 184. The charge conditioner 192 is preferably a corona type, bi-polar device. The APMA 196 is a particle mass classifier. It transmits aerosol particle within a set mass range. APMA 196 voltage is controlled by the high voltage module 208. An example module 208 is provided by XP Power, Inc. The PAMS 200 is a particle size classifier. It preferably comprises a differential mobility analyzer (DMA) 216 and a high voltage module 220. The PAMS 200 controls DMA 216 flow and charge conditioner voltage control. The CPC 204 functions as a particle detector. An example PLC 212 is provided by Horner, Inc. It is used for voltage control and data collection. The PLC 212 steps through DMA 216 voltages at each APM 196 voltage set point. It counts particles detected by the CPC 204.

Figure 11:
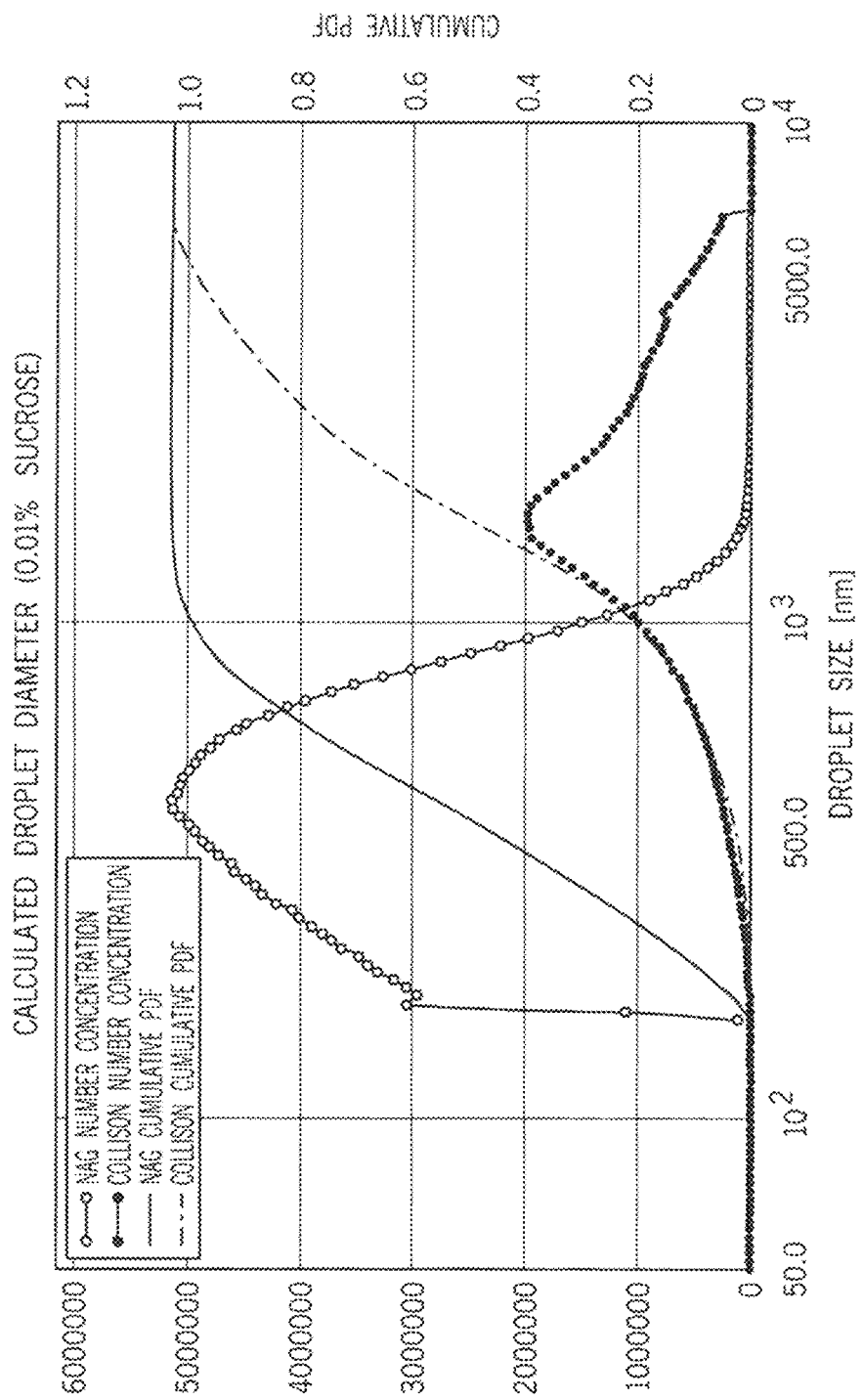
FIG. 11 shows the calculated droplet diameter with a relatively small size distribution with reduced large droplet generation.

Referring to FIG. 11, the Nano aerosol generator produces a relatively small droplet size distribution with reduced large droplet generation. This reduces the size of the particle composed of precipitated non-volatile residue. It also reduces the probability of coincident particles within a droplet (scales with diameter$^3$.

Figure 12A:
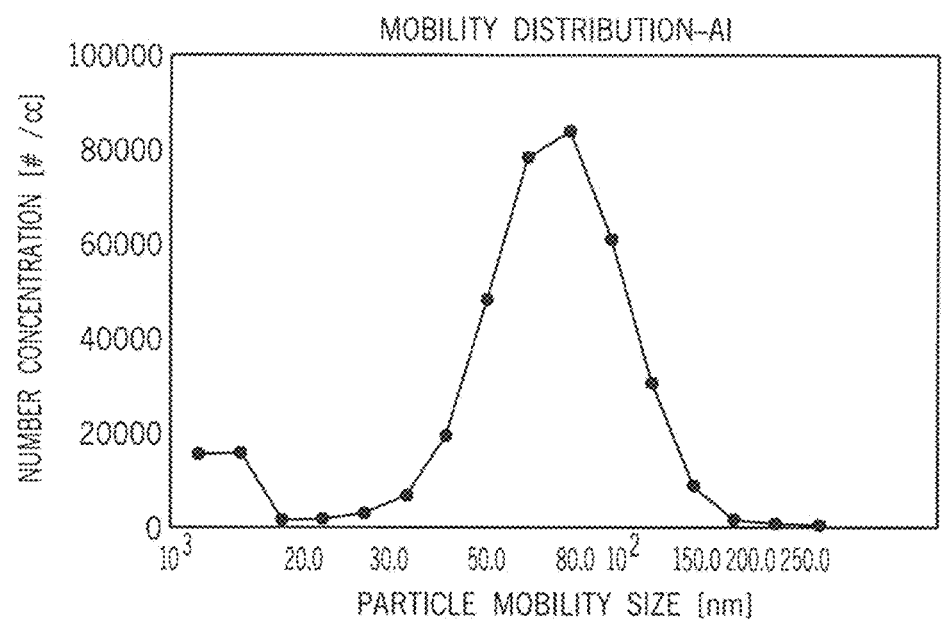
FIGS. 12 A-B are a graph aid contour plot (or heat map) respectively, showing mobility distribution and mass to charge ratio vs. particle size for Raw Al.
Figure 12B:
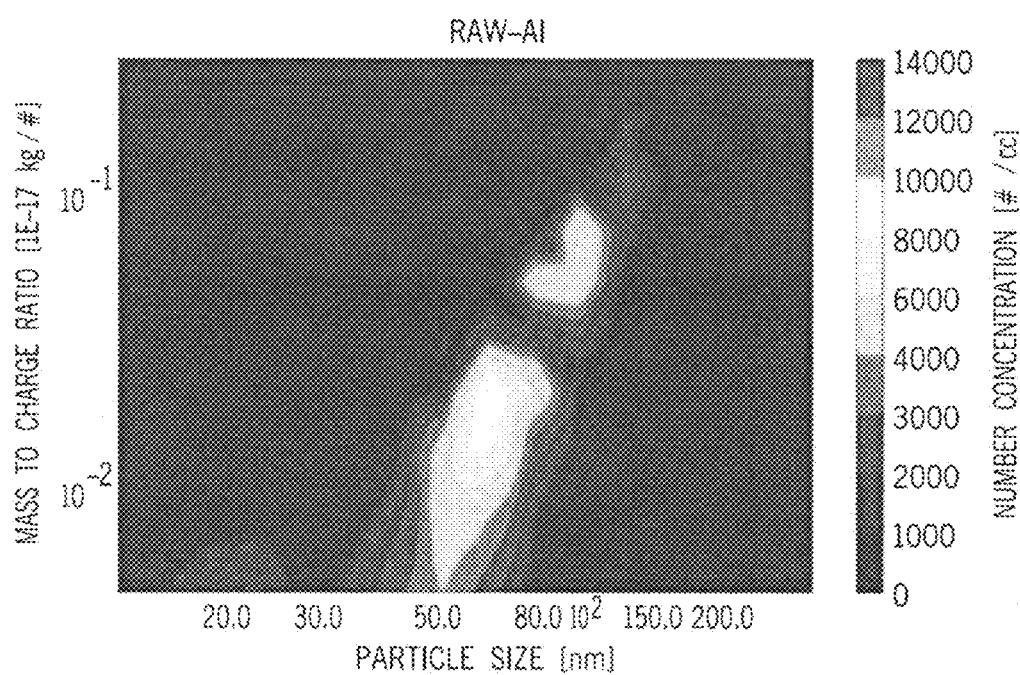
Figure 13A:
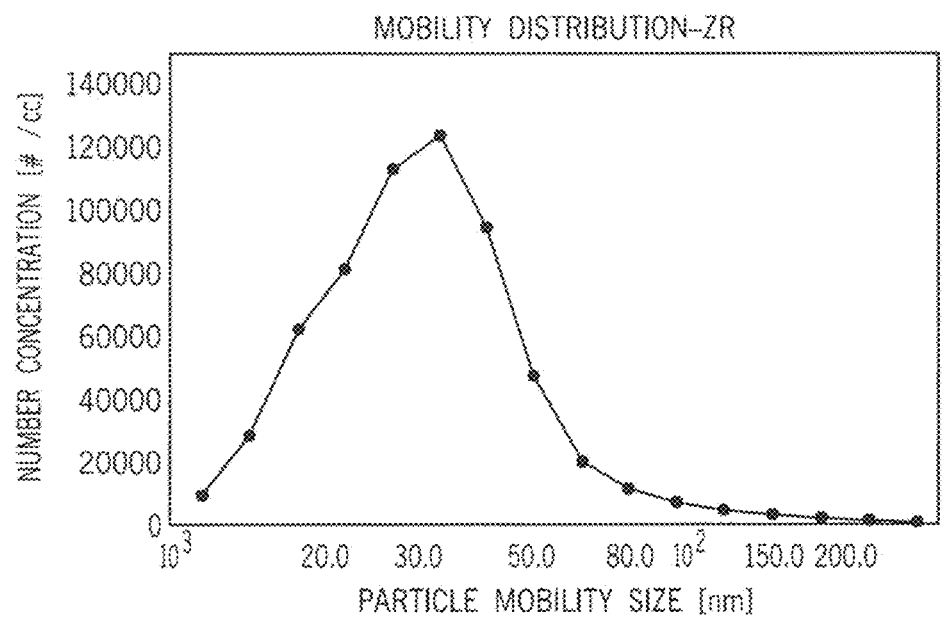
FIG. 13 A-B show mobility distribution and mass to charge ratio vs. particle size for Raw Zr.
Figure 13B:
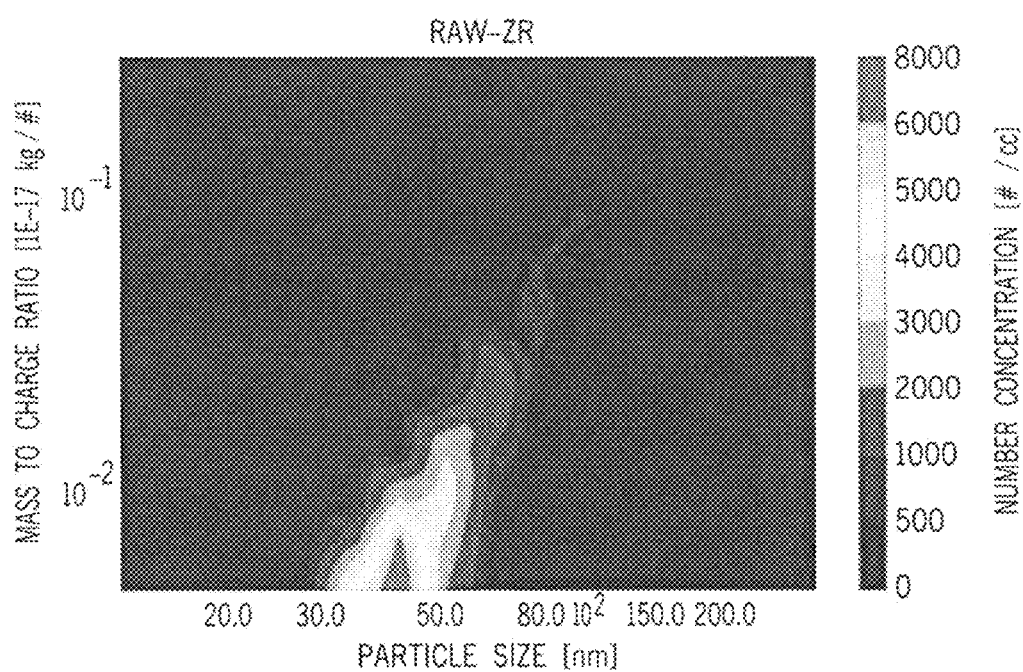
Figure 14A:
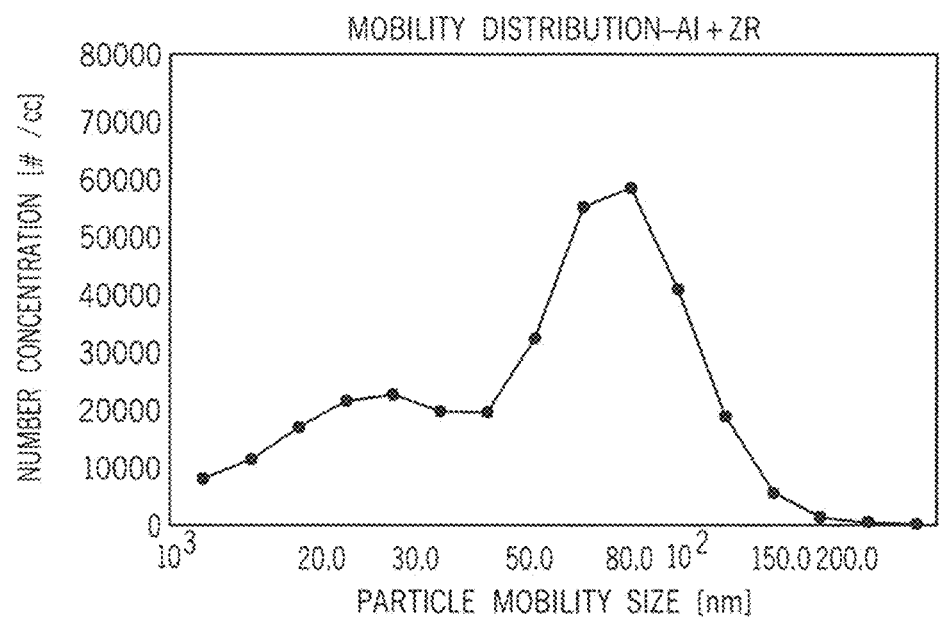
FIGS. 14 A-B show mobility distribution and mass to charge ratio vs. particle size for Raw Al+Zr.
Figure 14B:
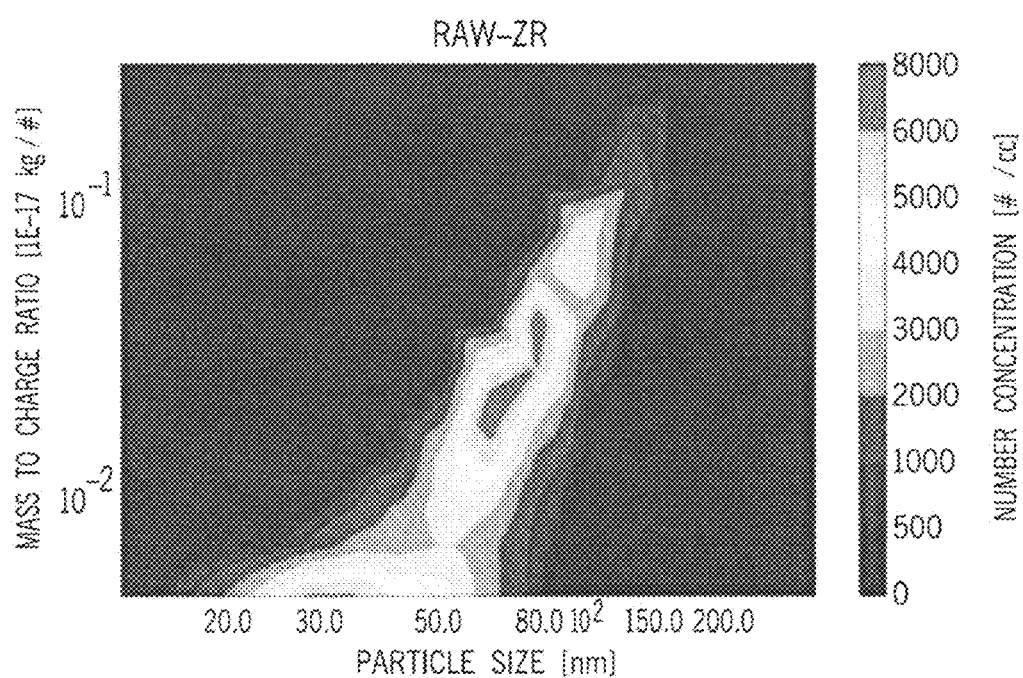
Figure 15:
FIG. 15 is a data inversion algorithm for correcting for DMA and APM transfer functions, CPC detection efficiency, and charge distribution.

A data inversion algorithm is used to correct for DMA and APM transfer functions, CPC detection efficiency, and charge distribution. The algorithm is shown in FIG. 15.
In the algorithm:
z=electrical charge state (number of charges)
dp=particle diameter
mp=particle mass
Lambda=transfer function of particle size classifier (the transfer function if a probability distribution of transmission as a function of size)
i=index for discrete selected electrical mobilities (DMAS voltage setting)
Omega=transfer function of particle mass classifier
j=index for discrete selected mass (APM voltage setting)
epsilon_CPC=size dependent detection efficiency of the particle counter
epsilon_t=size dependent detection efficiency of the system (primarily due to particle loss through diffusion to, and deposition onto, tubing walls)
f_z=charge distribution of particles leaving the charge conditioner (the ionization source for the charge conditioner can be radioactive, soft x-ray, corona discharge, or similar)
N=number concentration FIGS. 12 A-B, 13 A-B, and 14 A-B are graphs and contour plots which illustrate mobility distribution and mass to charge ratio vs. particle size for Raw Al, Zr, and Zr+Al, respectively. Unique aerosol populations can be identified and their individual size distributions can be plotted by manually selecting the appropriate data regions after plotting of data utilizing the in version formula above.

In summary, the apparatus of the colloid particle size-mass distribution measurement system includes a colloid sample input; a nebulizer communicatively connected to the colloid sample input; a particle classifier communicatively connected to the nebulizer; and a particle defector communicatively connected to the particle classifier. The particle size classifier may be a size classifier or a mass classifier. It preferably includes an online dilution module. It may include both a particle size classifier and a particle mass classifier, wherein the size classifier may be disposed between the nebulizer and the mass classifier or between the mass classifier and the particle detector. Other variations are set forth both above and in the claims.

The method of measuring the particle size-mass distribution of a colloid of the invention comprises, in summary, the steps of (a) providing an colloid sample, (b) nebulizing the sample, (c) classifying the fluid by size, mass, or both, and (d) detecting particles, preferably by condensation particle counting. Variations of this method are disclosed above.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A colloid particle size-mass distribution measurement apparatus comprising:
    a colloid sample input;
    a nebulizer communicatively connected to the colloid sample input;
    a particle mass classifier communicatively connected to the nebulizer; and
    a particle detector communicatively connected to the particle classifier.

2. The colloid particle size-mass distribution measurement apparatus of claim 1, wherein the particle classifier is a particle size classifier.

3. The colloid particle size-mass distribution measurement apparatus of either of claim 2 or 1, further comprising an online dilution module communicatively connected between the colloid sample input and the nebulizer, the online dilution module including an ultra pure water inlet.

4. The colloid particle size-mass distribution measurement apparatus of claim 3, wherein the colloid sample input comprises a sample container connected to a sample pump, and wherein the online dilution module comprises a plurality of turbulent mixers communicatively connected in line between the sample pump and the nebulizer, the ultra pure water inlet being connected to at least one turbulent mixer.

5. The colloid particle size-mass distribution measurement apparatus of claim 1, further comprising a particle size classifier disposed between the nebulizer and the particle mass classifier.

6. The colloid particle size-mass distribution measurement apparatus of claim 1, further comprising a particle size classifier disposed between the particle mass classifier and the particle detector.

7. The colloid particle size-mass distribution measurement apparatus of either of claim 5 or 6, further comprising an online dilution module communicatively connected between the colloid sample input and the nebulizer, the online dilution module including an ultra pure water inlet.

8. The colloid particle size-mass distribution measurement apparatus of claim 7, wherein the colloid sample input comprises a sample container connected to a sample pump, and wherein the online dilution module comprises a plurality of turbulent mixers communicatively connected in line between the sample pump and the nebulizer, the ultra pure water inlet being connected to at least one turbulent mixer.

9. The colloid particle size-mass distribution measurement apparatus of claim 1, wherein the colloid sample input comprises a sample container connected to a sample pump.

10. The colloid particle size-mass distribution measurement apparatus of claim 1, wherein the nebulizer is a nano-aerosol generator.

11. The colloid particle size-mass distribution measurement apparatus of claim 1, wherein the particle mass classifier is an aerosol particle mass analyzer.

12. The colloid particle size-mass distribution measurement apparatus of claim 1, wherein the particle detector is a condensation particle counter.

13. The colloid particle size-mass distribution measurement apparatus of claim 1, further comprising an aerosol dryer communicatively connected to an output of the nebulizer.

14. The colloid particle size-mass distribution measurement apparatus of claim 1, further comprising a corona type, bi-polar charge conditioner communicatively connected between the nebulizer and the particle mass classifier.

15. The colloid particle size-mass distribution measurement apparatus of claim 1, further comprising a differential mobility analyzer connected between the particle mass classifier and particle detector.

16. The colloid particle size-mass distribution measurement apparatus of claim 1, further comprising a controller communicatively connected to at least the particle mass classifier.

17. A colloid particle size-mass distribution measurement apparatus comprising:
    a. a colloid sample input;
    b. an online dilution module connected to the colloid sample input;
    b. a nebulizer communicatively connected to the online dilution module;
    c. a particle mass classifier communicatively connected to the nebulizer;
    d. a condensation particle counter particle detector communicatively connected to the particle classifier, and
    e. a controller communicatively connected to at least the particle mass analyzer.

18. A colloid particle size-mass distribution measurement apparatus comprising:
    a. a colloid sample input;

b. an online dilution module connected to the colloid sample input;
c. a nano-aerosol generator communicatively connected to the online dilution module;
d. an aerosol dryer communicatively connected to the nano-aerosol generator;
e. a charge conditioner communicatively connected to the aerosol dryer;
f. a particle mass classifier communicatively connected to the charge conditioner;
g. a condensation particle counter particle detector communicatively connected to the particle classifier, and
h. a controller communicatively connected to at least the particle mass analyzer.

* * * * *